(12) United States Patent
Mostowfi et al.

(10) Patent No.: US 9,346,049 B2
(45) Date of Patent: May 24, 2016

(54) MICROFLUIDIC CHIP FOR MEASURING ASPHALTENE CONTENT OF CRUDE OIL

(71) Applicant: Schlumberger Technology Corporation, Sugar Land, TX (US)

(72) Inventors: Farshid Mostowfi, Edmonton (CA); Abdel M. Kharrat, Edmonton (CA); Philip James Homewood, Enfield (GB); Joseph Samuel Baddeley, Cambridge (GB); Marc Schneider, Walheim (DE)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 14/679,539

(22) Filed: Apr. 6, 2015

(65) Prior Publication Data

US 2015/0209782 A1 Jul. 30, 2015

Related U.S. Application Data

(62) Division of application No. 14/347,641, filed as application No. PCT/US2013/027364 on Feb. 22, 2013.

(60) Provisional application No. 61/602,531, filed on Feb. 23, 2012.

(51) Int. Cl.
*B01L 3/00* (2006.01)
*G01N 33/28* (2006.01)
(Continued)

(52) U.S. Cl.
CPC ......... *B01L 3/502715* (2013.01); *B01L 3/5027* (2013.01); *B01L 3/502753* (2013.01);
(Continued)

(58) Field of Classification Search
CPC . G01N 33/2823; G01N 21/05; G01N 21/314; G01N 21/85; G01N 25/02; G01N 33/2847; G01N 21/25; G01N 21/59; G01N 21/83; G01N 31/16; G01N 33/28; B01L 3/5027; B01L 2300/0654; B01L 2300/0887; B01L 2400/0463; B01L 2400/0487; B01L 3/502784; B01L 9/527; B01L 2300/0681; B01L 2300/0816; B01L 2300/0867; B01L 2300/0883; B01L 3/502753
USPC ................. 422/502–504, 82.09, 224, 606; 210/416.5, 745; 356/326, 70
See application file for complete search history.

(56) References Cited

U.S. PATENT DOCUMENTS

| | | | |
|---|---|---|---|
| 4,843,247 A | 6/1989 | Yamazoe et al. |
| 5,266,800 A | 11/1993 | Mullins |

(Continued)

FOREIGN PATENT DOCUMENTS

| | | |
|---|---|---|
| EP | 1813348 A1 | 8/2007 |
| WO | 2011/151746 A1 | 12/2011 |
| WO | 2004/022233 A1 | 3/2014 |

OTHER PUBLICATIONS

International Search Report and Written Opinion of PCT/US2013/027364 mailing date Jun. 2, 2013.

(Continued)

*Primary Examiner* — Dean Kwak
(74) *Attorney, Agent, or Firm* — Daren C. Davis; Wayne I. Kanak (57) ABSTRACT

A system for measuring asphaltene content of crude oil, includes a microfluidic chip, the microfluidic chip having a crude oil sample inlet port, a solvent port, a mixer and reactor section in fluid communication with the crude oil sample inlet port and the solvent port, and a filter in fluid communication with the mixer and reactor section, the filter having an inlet side and an outlet side, a waste port in fluid communication with the inlet side of the filter, and a product port in fluid communication with the outlet side of the filter. The system further includes an optical cell in fluid communication with the product port.

5 Claims, 8 Drawing Sheets

(51) Int. Cl.
*G01N 21/59* (2006.01)
*G01N 21/05* (2006.01)
*B01D 24/00* (2006.01)

(52) U.S. Cl.
CPC .............. *G01N21/05* (2013.01); *G01N 21/59* (2013.01); *G01N 33/2823* (2013.01); *B01L 2300/0681* (2013.01); *B01L 2300/0816* (2013.01); *B01L 2300/0867* (2013.01); *B01L 2300/0883* (2013.01); *B01L 2300/12* (2013.01)

(56) References Cited

U.S. PATENT DOCUMENTS

| | | |
|---|---|---|
| 6,992,768 B2 | 1/2006 | Dong et al. |
| 8,269,961 B2 | 9/2012 | Mostowfi et al. |
| 2009/0311157 A1* | 12/2009 | Steel et al. ............... 423/249 |
| 2010/0136698 A1 | 6/2010 | Dadic et al. |
| 2010/0210008 A1* | 8/2010 | Strand et al. ............ 435/287.1 |

OTHER PUBLICATIONS

Bowden, Stephen A., et al. "Determination of the asphaltane and carboxylic acid content of a heavy oil using a microfluidic device," LAb on a chip, 2009, vol. 9, No. 6, pp. 828-832.

Van Dam R M et al, "Automated Microfluidic-chip-based Stand-alone Instrument for the Synthesis of Radiopharamaceuticals on Human-dose scales", XP-002747336, 2007 Insti Nanotechnology Confererence and Trade Show, vol. 3, pp. 300-303.

Supplementary European Search Report for corresponding European Application Serial No. EP 13752264.5 dated Nov. 19, 2015, 5 pages.

* cited by examiner

MICROFLUIDIC CHIP FOR MEASURING ASPHALTENE CONTENT OF CRUDE OIL

CROSS-REFERENCE TO RELATED APPLICATIONS

This application claims priority from U.S. Non-Provisional application Ser. No. 14/347,641 filed on Feb. 22, 2013, International Application No. PCT/US2013/0273664 filed on Feb. 22, 2013, and U.S. Provisional Application No. 61/602,531, filed on Feb. 23, 2012, the disclosures of which are incorporated by reference herein in their entireties.

BACKGROUND

The measurement of asphaltene content of a hydrocarbon reservoir fluid is a common aspect of oil production, transportation, and refining. Because asphaltenes are not generally well defined and not well understood, numerous methods have been developed for characterizing and quantifying asphaltenes in such reservoir fluids. Conventional methods, however, require large quantities of sample reservoir fluids and solvents, large glass vessels, and many other instruments for proper extraction of the asphaltenes. Typically, the quantification of asphaltenes is performed by weighing asphaltenes extracted from the reservoir fluid, generally must be performed in a laboratory environment, and require significant lengths of time to complete.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, the disclosed subject matter provides a system for measuring asphaltene content of crude oil. The system includes a microfluidic chip and an optical cell. The microfluidic chip comprises a sample inlet port, a solvent port, and a mixer and reactor section in fluid communication with the sample inlet port and the solvent port. The microfluidic chip further includes a filter in fluid communication with the mixer and reactor section, the filter having an inlet side and an outlet side. The microfluidic chip further includes a waste port in fluid communication with the inlet side of the filter and a product port in fluid communication with the outlet side of the filter. The optical cell is in fluid communication with the product port.

In another aspect, the disclosed subject matter provides a microfluidic chip. The microfluidic chip includes a sample inlet port, a solvent port, and a mixer and reactor section in fluid communication with the sample inlet port and the solvent port. The microfluidic chip further includes a filter in fluid communication with the mixer and reactor section, the filter having an inlet side and an outlet side. The microfluidic chip further comprises a waste port in fluid communication with the inlet side of the filter and a product port in fluid communication with the outlet side of the filter.

In yet another aspect, the disclosed subject matter provides a microfluidic chip. The microfluidic chip includes an upper portion defining a sample inlet port, a solvent port, a waste port, a product port, a mixing channel, and a reactor channel, the mixing channel being in fluid communication with the sample inlet port, the solvent port, and the reactor channel. The microfluidic chip further includes an intermediate portion defining a further channel in fluid communication with the reactor channel. The microfluidic chip further includes a membrane filter in fluid communication with the further channel, the membrane filter having an inlet side and an outlet side. The waste port is in fluid communication with the inlet side of the membrane filter and the product port is in fluid communication with the outlet side of the membrane filter. The desired filtration may also be achieved by other means such as a porous structure built into the microfluidic chip, settling chamber, or a centrifugal separator.

BRIEF DESCRIPTION OF THE DRAWINGS

Embodiments of the disclosed subject matter of the application are described with reference to the following figures. The same numbers are used throughout the figures to reference like features and components.

While the disclosed subject matter is susceptible to various modifications and alternative forms, specific embodiments thereof have been shown by way of example in the drawings and are herein described in detail. It should be understood, however, that the description herein of specific embodiments is not intended to limit the disclosed subject matter of the application to the particular forms disclosed, but on the contrary, the intention is to cover all modifications, equivalents, and alternatives falling within the scope of the disclosed subject matter as defined by the appended claims.

DETAILED DESCRIPTION

Illustrative embodiments of the disclosed subject matter of the application are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

The disclosed subject matter of the application relates to an apparatus for measuring the asphaltene content of a reservoir fluid, such as crude oil.

Generally, asphaltenes are the heaviest and most polar components in crude oil. The asphaltene fraction of a crude oil sample is generally defined as the fraction that is insoluble in an alkane, such as, for example, n-heptane, but soluble in an aromatic hydrocarbon, such as toluene. The deasphalted fraction of crude oil is commonly referred to as the maltene fraction. Asphaltenes typically exhibit significant optical absorbance or optical density in the visible light spectrum, while maltenes exhibit less optical absorbance or optical density in the visible light spectrum than asphaltenes. Considering crude oil as a combination of asphaltenes and maltenes, with the asphaltene fraction and the maltenes fraction of a crude oil sample each exhibiting a particular optical density or coloration, the linear addition of the density of each fraction results in the optical density or coloration of the crude oil sample. Comparison and calculation of the optical densities of crude oils and the crude oil fractions, that is, the asphaltenes and maltenes, is performed at substantially equal concentrations. For example, if a fraction, such as an asphaltene fraction or a maltenes fraction, is extracted from a crude oil sample, the extracted volume is replaced by a transparent solvent.

Figure 1:
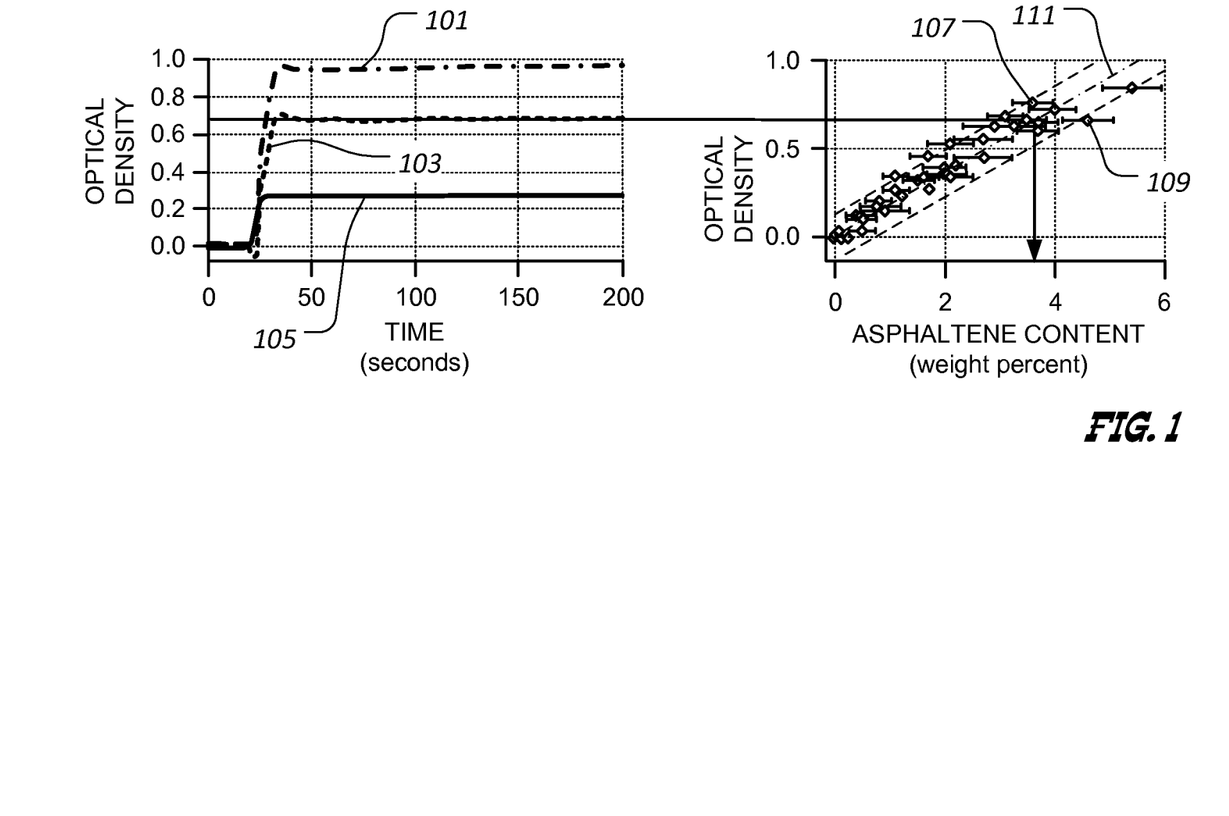
FIG. 1 is a graphical representation illustrating a correlation model.

The apparatus and system disclosed herein is used to indirectly determine the optical spectrum of the asphaltene fraction of a crude oil sample by subtracting the optical spectrum of the maltenes fraction from the optical spectrum of the crude oil sample. The asphaltene fraction is precipitated from the crude oil sample and filtered, leaving the maltenes fraction. Precipitation and measurements are performed within a microfluidic system on generally continuous fluid streams that are maintained for a sufficiently long period of time to allow representative and stable optical density measurements to be obtained. An example of such a determination is graphically shown in FIG. 1. In the optical density versus time graph shown on the left of FIG. 1, a line 101 graphically represents the optical density of a crude oil sample at a known wavelength. Line 103 graphically represents the optical density of an asphaltene fraction of the crude oil sample and line 105 graphically represents the optical density of a maltenes fraction of the crude oil sample. The optical density of the asphaltene fraction of the crude oil sample at the known wavelength is determined by subtracting the optical density of the maltene fraction of the crude oil sample from the optical density of the crude oil sample including both asphaltenes and maltenes. The optical density versus asphaltene content graph shown on the right of FIG. 1 represents a correlation model generated using many different samples of crude oil. For example, data point 107 represents the optical density of the asphaltene fraction of a particular crude oil sample, while data point 109 represents the optical density of the asphaltene fraction of another, different particular crude oil sample. Line 111 represents a linear fit of the optical density versus asphaltene content data. Thus, the optical density of the asphaltene fraction of a particular crude oil sample, for example as represented by line 103, can be used to determine the asphaltene content of the particular crude oil sample within a predetermined tolerance range.

Figure 2:
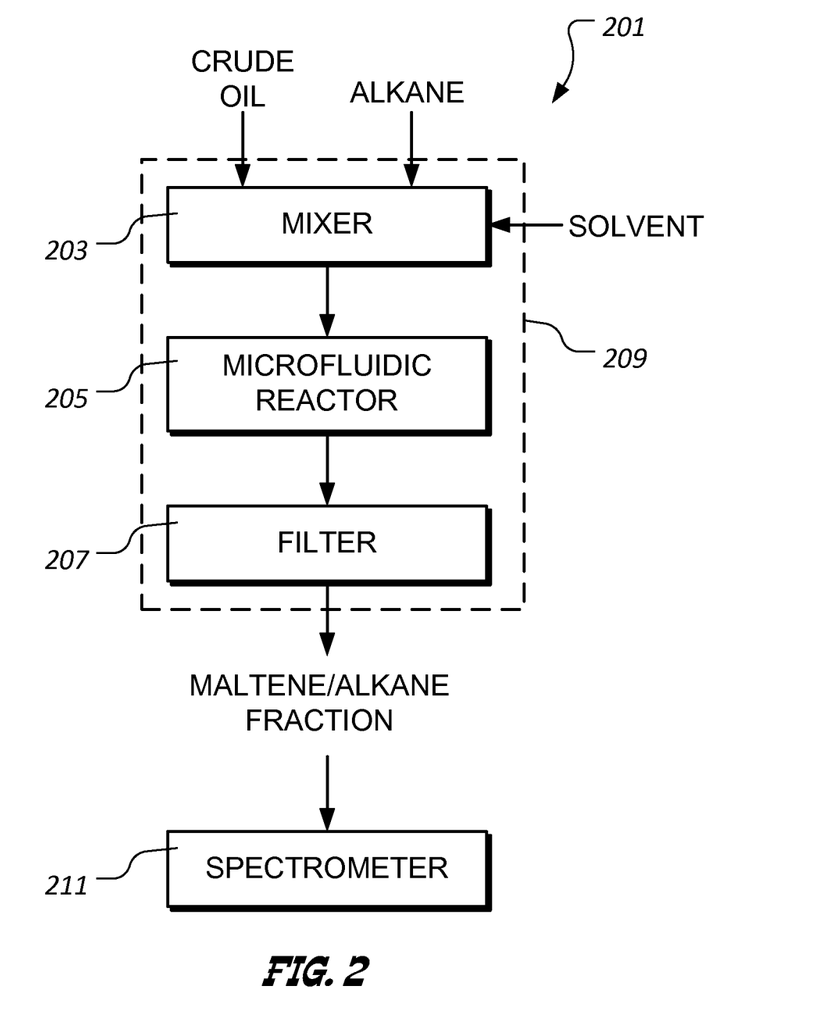
FIG. 2 is a schematic representation of a system for determining the optical density of asphaltenes in a crude oil sample.

FIG. 2 is a graphical representation of a system 201 for determining the optical density of asphaltenes in a crude oil sample. In the illustrated embodiment, a mixer 203, for example a microfluidic mixer, is in fluid communication with a microfluidic reactor 205. Microfluidic reactor 205 is operably associated with a filter 207, for example, a membrane filter. Crude oil and an alkane, such as n-heptane, are introduced into mixer 203 wherein the crude oil and the alkane are mixed. The mixture is communicated into microfluidic reactor 205, wherein the asphaltene fraction is precipitated from the crude oil by the alkane, such that the asphaltene precipitate is dispersed in the maltene fraction. The maltene/precipitated asphaltene mixture is communicated to filter 207, which filters out the asphaltene precipitate, allowing the maltene fraction to pass through. Mixer 203, microfluidic reactor 205, and filter 207 are operatively associated to form a microfluidic chip 209. System 201 further comprises a spectrometer 211 in fluid communication with filter 207. The maltene fraction is communicated to spectrometer 211, wherein the optical density of the maltene fraction is determined.

In one embodiment, system 201 of FIG. 2 is configured such that, a solvent, such as toluene, can be selectively introduced into mixer 203 to aid in moving the crude oil through system 201 for the purpose of determining the optical density of the crude oil. The crude oil and the solvent are communicated though mixer 203, microfluidic reactor 205, and filter 207 to spectrometer 211, wherein the optical density of the crude oil is determined.

Figure 3:
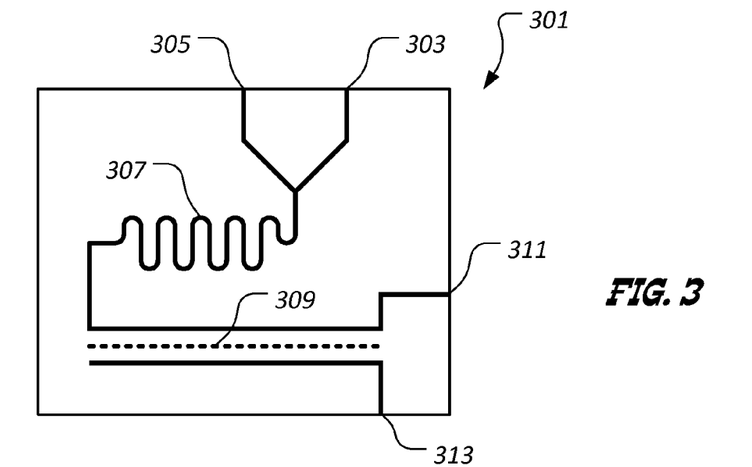
FIG. 3 is a schematic representation of a first illustrative embodiment of a microfluidic chip.

FIG. 3 depicts a schematic representation of an illustrative embodiment of a microfluidic chip 301, such as microfluidic chip 209, shown in FIG. 2. In the illustrated embodiment, microfluidic chip 301 includes a crude oil sample inlet port 303 and a solvent port 305. Solvent port 305 can be used to introduce a solvent, such as toluene, or an alkane, such as n-heptane, to microfluidic chip 301 depending upon the particular operation of microfluidic chip 301. Each of sample inlet port 303 and solvent port 305 are in fluid communication with a mixer and reactor section 307, which comprises one or more serpentine channels. In the mixer portion of mixer and reactor section 307, the sample and the fluid introduced via solvent port 305 are mixed. In the reactor portion of mixer and reactor section 307, asphaltene in the sample precipitates as asphaltene flock disposed in maltenes when the crude oil sample is mixed with an alkane. Microfluidic chip 301 further comprises a filter 309, such as a membrane filter, which is in fluid communication with mixer and reactor section 307. Filter 309 is configured to allow the maltenes to pass therethrough but not to allow the asphaltene flock to pass therethrough. The asphaltene flock can be flushed from microfluidic chip 301 via a waste port 311 using a solvent introduced via solvent port 305. The maltenes and residual alkane or solvent are collected from microfluidic chip 301 via a product port 313.

Figure 4:
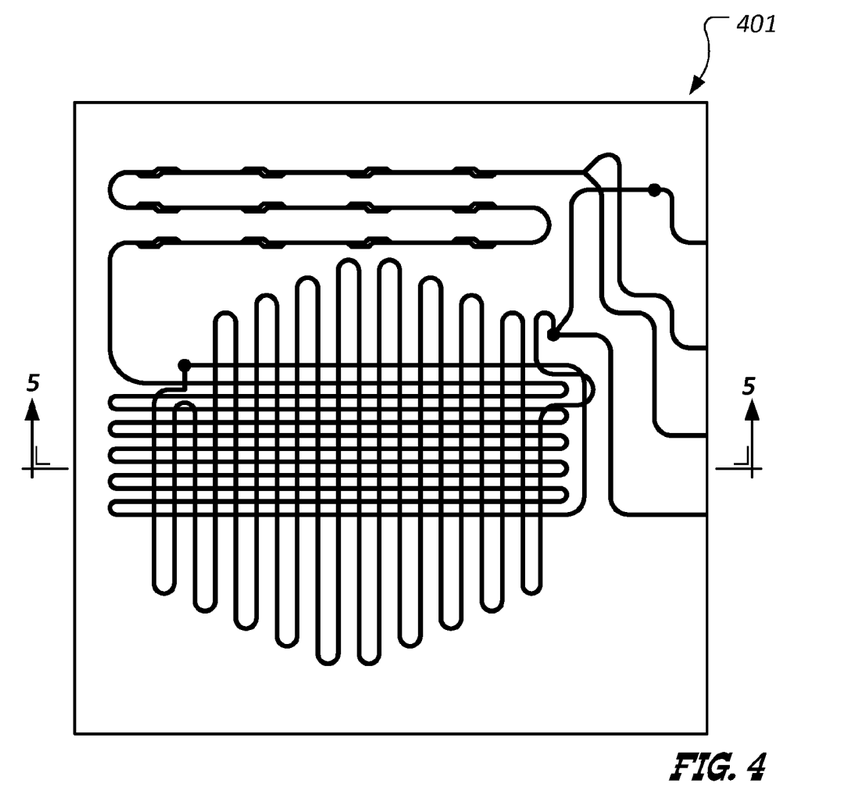
FIG. 4 is a top, plan view of a second illustrative embodiment of a microfluidic chip.
Figure 5:
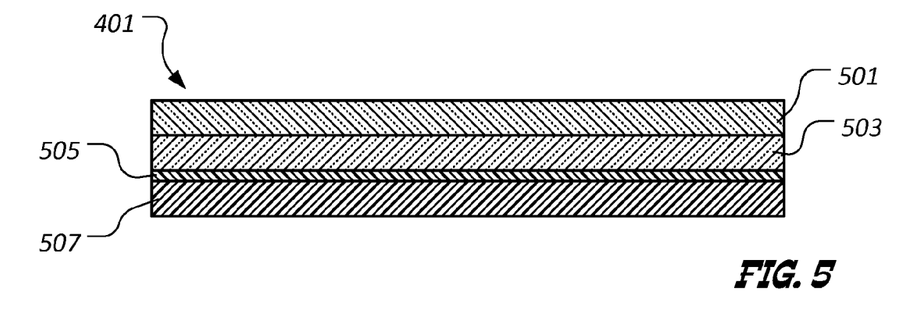
FIG. 5 is a sectional, elevational view of the microfluidic chip of FIG. 4.
Figure 6:
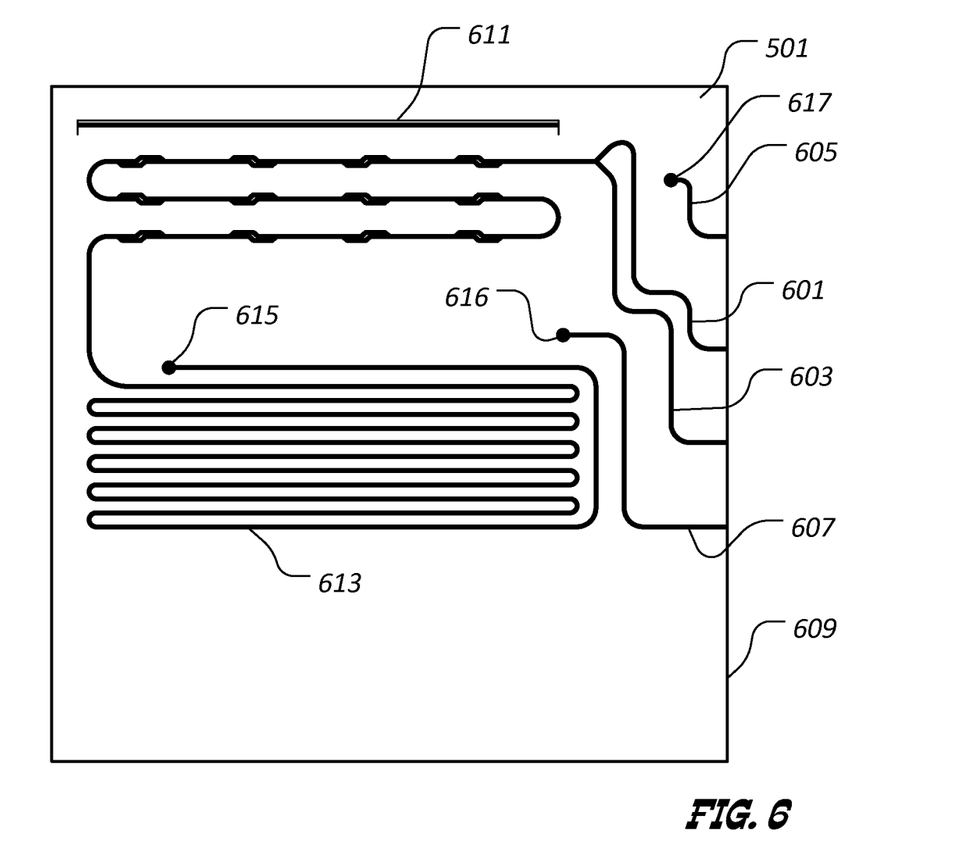
FIG. 6 is a top, plan view of an upper portion of the microfluidic chip of FIG. 4.
Figure 7:
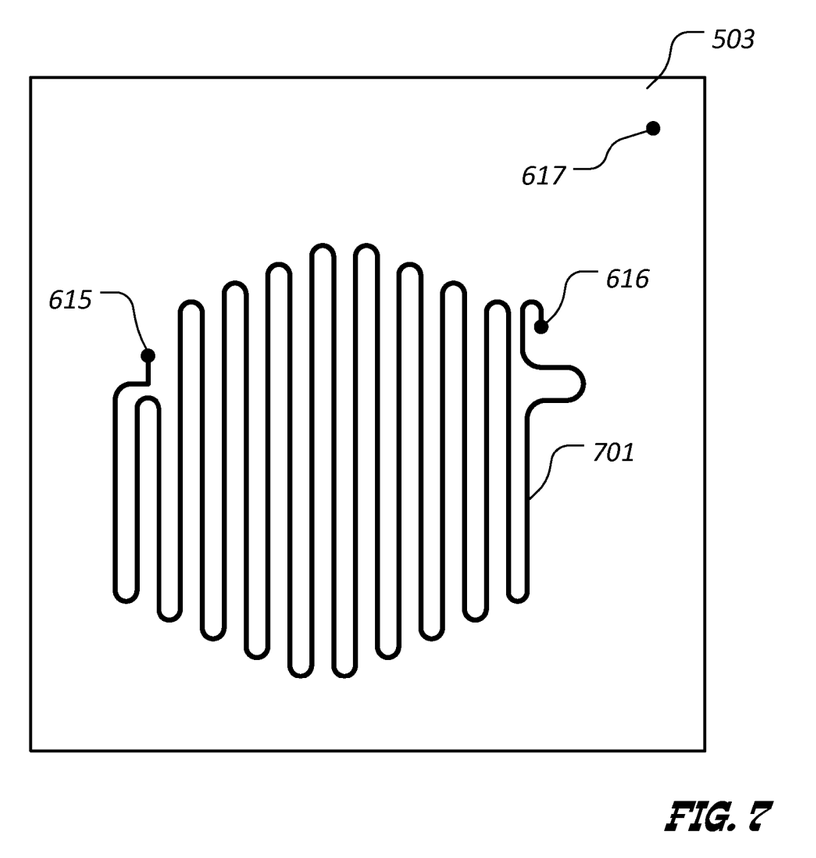
FIG. 7 is a top, plan view of an intermediate portion of the microfluidic chip of FIG. 4.
Figure 8:
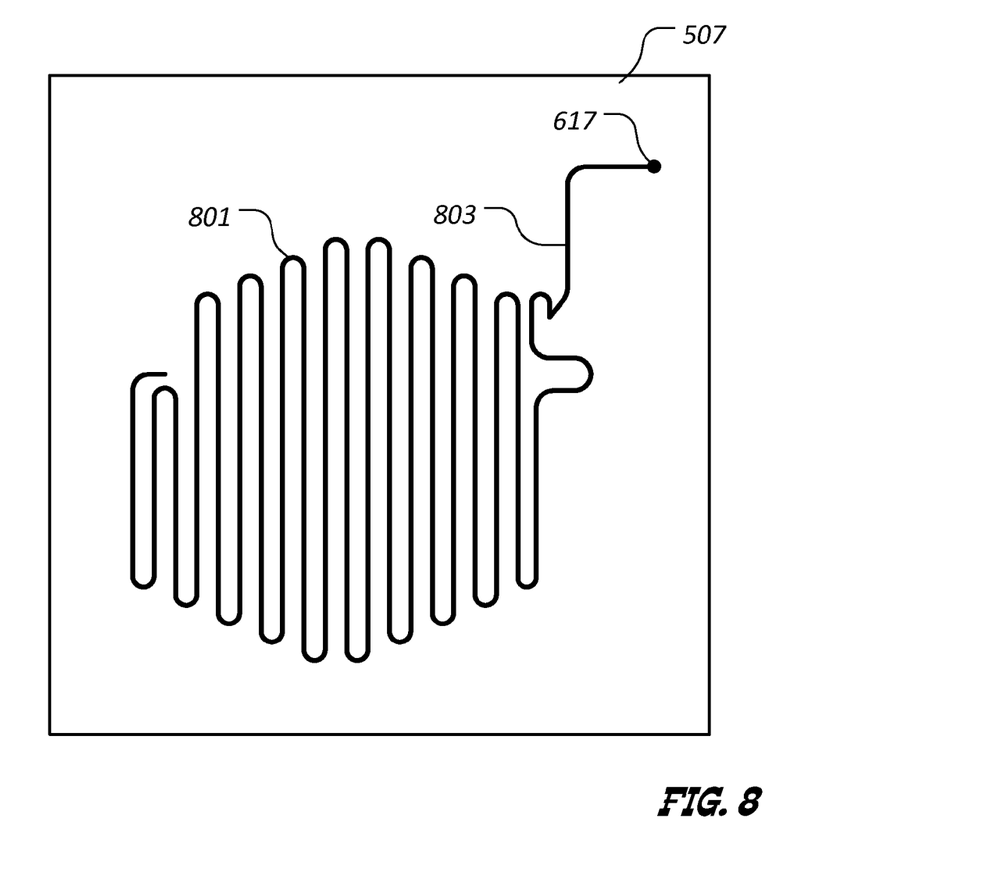
FIG. 8 is a top, plan view of a lower portion of the microfluidic chip of FIG. 4.

FIGS. 4-8 depict a microfluidic chip 401, which is a particular implementation of microfluidic chip 301 of FIG. 3. FIG. 4 is a top, plan view of microfluidic chip 401, while FIG. 5 is a sectional, elevational view of microfluidic chip 401. As can be seen in FIG. 5, microfluidic chip 401 comprises an upper portion 501, an intermediate portion 503, a filtration membrane 505, and a lower portion 507. Filtration membrane 505 is disposed between intermediate portion 503 and lower portion 507. Each of portions 501, 503, and 507 define certain channels for transporting crude oil and/or other fluids through microfluidic chip 401. Crude oil and solvent are introduced into upper portion 501 of microfluidic chip 401, wherein the crude oil and solvent are mixed to induce separation of asphaltenes from the crude oil. The asphaltenes are filtered from the mixture by filtration membrane 505, allowing the maltenes and the remaining alkane or solvent to pass therethrough into lower portion 507. The maltenes and remaining alkane or solvent are then routed from microfluidic chip 401 via lower portion 507 and upper portion 501. To better illustrate the particular aspects of microfluidic chip 401, FIG. 6 depicts channels defined only in upper portion 501, FIG. 7 depicts channels defined only in intermediate portion 503, and FIG. 8 depicts channels defined only in lower portion 507.

Referring now to FIG. 6, upper portion 501 of microfluidic chip 401 defines a sample inlet port 601, a solvent port 603, a product port 605, and a waste port 607. It should be noted that a solvent or an alkane may be introduced into microfluidic chip 401 via solvent port 603 depending upon the particular operation of microfluidic chip 401. Sample inlet port 601 and solvent port 603 are channels defined by upper portion 501 that lead from an edge 609 of upper portion 501 to a mixing channel 611 defined by upper portion 501. In the illustrated embodiment, mixing channel 611 is a microfluidic mixing channel, although other types of mixing devices are contemplated. Mixing channel 611 is in fluid communication with a first serpentine channel 613, which routes fluids through upper portion 501 of microfluidic chip 401 to a transfer port 615, which is in fluid communication with a second serpentine channel 701 (FIG. 7) defined by intermediate portion 503.

Referring now to FIG. 7, intermediate portion 503 of microfluidic chip 401 defines a second serpentine channel 701, which routes fluids through intermediate portion 503 of microfluidic chip 401. First serpentine channel 613, shown in FIG. 6, defines a microfluidic reactor of microfluidic chip 401, while the length of second serpentine channel 701 determines the amount of asphaltenes that can be stored in microfluidic chip 401, and hence the amount of fluid that can be processed in one cycle. Within the microfluidic reactor, that is, within first serpentine channel 613, alkane introduced via solvent port 603 reacts with the sample fluid to cause asphaltene precipitation. The microfluidic reactor is sufficient in length to allow adequate time for asphaltene flock growth within the microfluidic reactor. Second serpentine channel 701 is in fluid communication generally entirely with filtration membrane 505, shown in FIG. 5. Thus, fluids flowing through second serpentine channel 701 are filtered by filtration membrane 505, such that fluids are allowed to pass through filtration membrane 505; however, particulates, such as asphaltene flock, are substantially retained by filtration membrane 505 and not allowed to pass therethrough. Second serpentine channel 701 is also connected to waste port 607 by transfer port 616.

Referring now to FIGS. 6 and 8, filtered fluid is collected in a filter channel 801, and then routed via a product channel 803, each defined by lower portion 507. In the illustrated embodiment, filter channel 801 exhibits substantially the same shape as second serpentine channel 701 of intermediate portion 503, shown in FIG. 7. Product channel 803 is in fluid communication with product port 605 via a transfer port 617. Transfer port 617 and product port 605 are each defined by upper portion 501. The filtered fluid is subsequently inspected, such as by using optical spectroscopy, to determine the optical density of the filtered fluid. Referring in particular to FIG. 6, waste, that is, the materials that do not pass through filtration membrane 505, are routed or flushed to waste port 607.

Referring in particular to FIG. 5, in one embodiment, upper portion 501 and intermediate portion 503 may comprise B 270® glass, available from SCHOTT North America, Inc. of Elmsford, N.Y., USA, fused silica, or the like. In one embodiment, upper portion 501 is generally about one millimeter thick and intermediate portion 503 is generally about two millimeters thick. Channels, ports, and the like defined by upper portion 501 and/or intermediate portion 503 are, in one embodiment, etched isotropically into the portions using, for example, a wet etching process. In one embodiment, one, some, or all of the channels, ports, and the like defined by upper portion 501 and intermediate portion 503 exhibit a plurality of depths, ranging from about 50 micrometers to about 250 micrometers and are produced using a multi-phase masking process. In one embodiment, lower portion 507 comprises polyetheretherketone (PEEK). In one embodiment, components of microfluidic chip 401 are mounted in a chip holder to locate the components relative to one another. In one embodiment, the chip holder includes a case housing highly-sprung bolts arranged about microfluidic chip 401. In a certain embodiment, when the bolts reach a "dead-stop", the clamp provides a compression force of about 600 Newtons to create a partial seal over filtration membrane 505. Thus, fluid passing through filtration membrane 505 is collected downstream of membrane 505 in the chip holder and guided to the output for analysis, while precipitated asphaltene flocks are held back and collect on the filtration membrane 505. In one embodiment, filtration membrane 505 comprises a polytetrafluoroethylene (PTFE) membrane with an average pore size of about 200 nm; however, membranes made of other materials and with different pore sizes are also contemplated.

Figure 9:
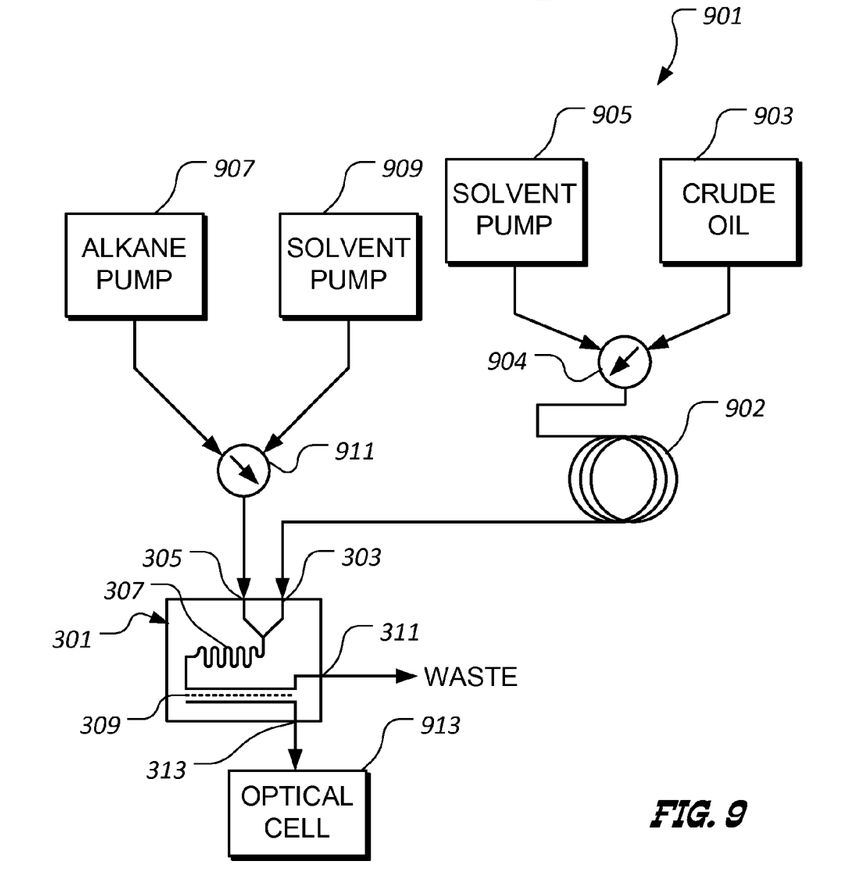
FIG. 9 is a schematic representation of a first illustrative embodiment of a system for measuring asphaltene content of crude oil.

FIG. 9 depicts a first illustrative embodiment of a system 901 for measuring asphaltene content of crude oil. System 901 is depicted as comprising microfluidic chip 301, shown in FIG. 3; however, system 901 may comprise microfluidic chip 401, shown in FIGS. 4-8, or any other configuration contemplated by the disclosure or its equivalent. In the illustrated embodiment, system 901 comprises a sample loop 902 in which a sample of crude oil is disposed after having been injected therein by, for example, a syringe pump, from crude oil sample reservoir 903 through a first switching valve 904. Sample loop 902 is in fluid communication with a first solvent pump 905 and sample inlet port 303 of microfluidic chip 301. System 901 further comprises an alkane pump 907 and a second solvent pump 909, each of which are selectively in fluid communication with solvent port 305 of microfluidic chip 301 via a second switching valve 911. In one embodiment, first solvent pump 905, second solvent pump 909, and alkane pump 907 are syringe pumps. System 901 further comprises an optical cell 913, such as a spectrometer, in fluid communication with product port 313 of microfluidic chip 301.

In a first particular operation of system 901, crude oil from sample reservoir 903 is first injected into sample loop 902 through first switching valve 904. Thereafter, the alignment of first switching valve 904 is switched and a solvent, such as toluene, is urged into sample loop 902 by first solvent pump 905 to urge the crude oil sample disposed therein into sample inlet port 303 of microfluidic chip 301. Second switching valve 911 is configured to allow second solvent pump 909 to urge a solvent, such as toluene, into solvent port 305 of microfluidic chip 301. As asphaltenes are soluble in such solvents, no asphaltene precipitation occurs; the crude oil sample is merely diluted. The diluted oil sample passes through filter 309 substantially in its entirety. In one embodiment, system 901 operates first solvent pump 905 and second solvent pump 909 to introduce the solvent into microfluidic chip 301 at a mixing ratio to dilute the crude oil sample sufficiently so that optical cell 913 can determine the optical density of the diluted crude oil. In this way, the same system 901 can be used to both determine the optical density of crude oil and the maltene component of crude oil.

In a second particular operation of system 901, a solvent, such as toluene, is urged into sample loop 902 by first solvent pump 905 to urge the crude oil sample disposed therein into sample inlet port 303 of microfluidic chip 301. Second switching valve 911 is then configured to allow alkane pump 907 to urge an alkane, such as n-heptane, into solvent port 305 of microfluidic chip 301. In one embodiment, system 901 operates first solvent pump 905 and alkane pump 907 to introduce the alkane into microfluidic chip 301 at a predetermined mixing ratio, such as 40 parts alkane to one part crude oil. The alkane and crude oil are mixed and the resulting flocculated asphaltenes are filtered, leaving maltenes and residual alkane material, as described herein regarding microfluidic chips 301 and 401. The maltenes and residual alkane material are then routed to optical cell 913 to determine their optical density.

Figure 10:
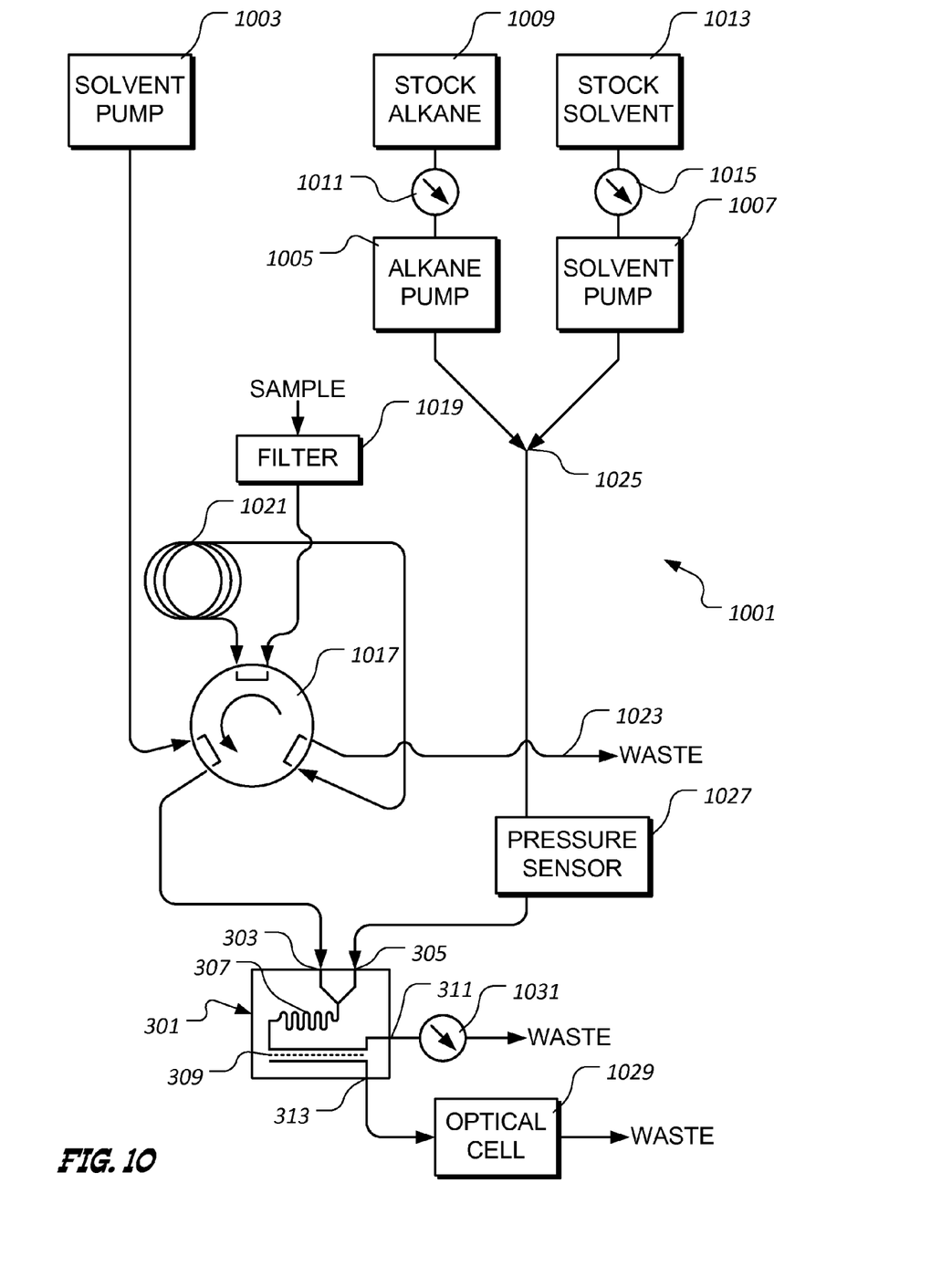
FIG. 10 is a schematic representation of a second illustrative embodiment of a system for measuring asphaltene content of crude oil.

FIG. 10 depicts a second illustrative embodiment of a system 1001 for measuring asphaltene content of crude oil. System 1001 is depicted as comprising microfluidic chip 301, shown in FIG. 3; however, system 1001 may comprise microfluidic chip 401, shown in FIGS. 4-8, or any other configuration contemplated by the disclosure or its equivalent. In the illustrated embodiment, system 1001 comprises a first solvent pump 1003, an alkane pump 1005, and a second solvent pump 1007. Alkane pump 1005 is operable to urge an alkane, such as n-heptane, therefrom, while second solvent pump 1007 is operable to urge a solvent, such as toluene, therefrom. In one embodiment, alkane pump 1005 is in fluid communication with a stock alkane reservoir 1009 via a valve 1011 and solvent pump 1007 is in fluid communication with a stock solvent reservoir 1013 via a valve 1015. In one embodiment, one or more of first solvent pump 1003, alkane pump 1005, and second solvent pump 1007 are syringe pumps, such as Mitos Duo XS pumps, available from The Dolomite Center Limited of Royston, Hertfordshire, UK. In one embodiment, valves 1011 and 1015 are part of the respective syringe pumps and are rated for pressures up to about six bars. In one embodiment, alkane pump 1005 and second solvent pump 1007 are configured to automatically fill when filling is needed. System 1001 further comprises a computer-controllable, six-port, two-way switching valve 1017, such as Cheminert Valve C22-3186, available from VICI Valco Instruments Co., Inc. of Houston, Tex., USA. In one embodiment, valve 1017 is rated for liquid pressures of about 16 bar.

Still referring to FIG. 10, when configured in a first position, valve 1017 places a filter 1019 in fluid communication with a crude oil sample loop 1021 and a waste port 1023. In one embodiment, filter 1019 comprises a dead-volume filter, such as a solvent filter assembly A-335, available from Upchurch Scientific, IDEX Health & Science LLC of Oak Harbor, Wash., USA. In such an embodiment, the filter includes a frit of about 10 micrometers, such as Semi-prep PEEK frit A-720, provided by Upchurch Scientific. An oil sample can be loaded manually, such as via a syringe, into sample loop 1021 via filter 1019 to remove large particulates before entering system 1001. In one embodiment wherein asphaltene content is to be measured, sample loop 1021 exhibits a volume of about 180 microliters. Additional crude oil may be required due to dead volume in filter 1019 and upstream of filter 1019 and for overfilling sample loop 1021. In one particular operation, about 250 microliters of crude oil is used to load sample loop 1021. First solvent pump 1003 is operable to urge a solvent, such as toluene, into sample loop 1021 via valve 1017 in a second position to urge a crude oil sample from sample loop 1021. Sample loop 1021 is in fluid communication with sample inlet port 303 of microfluidic chip 301 via valve 1017.

The outputs of alkane pump 1005 and second solvent pump 1007 are merged in a Y section 1025 and are both in fluid communication with a pressure sensor 1027, such as model 40PCXXXG2A, available from Honeywell Sensing and Control of Golden Valley, Minn., USA, such that the indicator "XXX" corresponds to the desired pressure range in pounds per square inch. Although pressure sensor 1027 is shown in FIG. 10 as being an in-line sensor, the scope of the disclosure encompasses embodiments wherein pressure sensor 1027 is a dead-end pressure sensor in fluid communication with a T-junction in the flow line. Pressure sensor 1027 functions to detect an overpressure of system 1001, such as may result from excessive asphaltene build up, so that the operation of system 1001 can be halted. Pressure sensor 1027 can also function so that fluid dispensing can be adjusted to maintain pressure levels within the pressure rating of system 1001. Alkane pump 1005 and second solvent pump 1007 are in fluid communication with solvent port 305 of microfluidic chip 301.

Referring still to FIG. 10, product port 313 of microfluidic chip 301 is in fluid communication with an optical cell 1029, operable to determine an optical density of fluid emitted from product port 313. In one embodiment, optical cell 1029 comprises an optical absorbance flow cell, such as a 2.5 mm optical path FIAlab SMA-Z-uvol cell with fused silica windows (SMA-Z-2.5-uvol), available from FIAlab Instruments, Inc. of Bellevue, Wash., USA. The optical flow cell is connected via fiber optics to a broadband light source based on a tungsten filament bulb, such as a model LS-1 light source available from OceanOptics, Inc. of Dunedin, Fla., USA, and to a broadband spectrometer, such as a model HR2000+ provided by OceanOptics, Inc. In one embodiment, the spectrometer is computer controlled. Waste port 311 of microfluidic chip 301 is in fluid communication with a switching valve 1031 to selectively allow fluid flow from waste port 311. In one embodiment, switching valve 1031 is a 2/2, on/off, direct lift solenoid valve, such as a model S-01540-03, available from Cole-Parmer Canada, Inc. of Montreal, Quebec, Canada. Switching valve 1031 inhibits flow therethrough during normal operation and allows flow during cleaning of filter 309 of microfluidic chip 301.

In certain embodiments, system 1001 utilizes tubing with 1/16-inch (1.6 mm) outer diameter and 1/4-28 flat bottom flangeless fittings. The tubing materials used, in some embodiments, are fluorinated ethylene propylene where high transparency is required and ethylene tetrafluoroethylene (Tefzel® available from E. I. du Pont de Nemours and Company of Wilmington, Del., USA) elsewhere due to its more rigid structure. In certain embodiments, the inner diameter of such tubing is 0.01 inch (0.25 mm) for minimal dead volume on all feed and product lines and 0.03 inch (0.76 mm) for waste lines, in order to reduce flow resistance.

In one particular operation of system 1001, system 1001 is purged. First solvent pump 1003, alkane pump 1005, and second solvent pump 1007 are operated at high flow rates and valves 1011, 1015, 1017, and 1031 are operated to remove air bubbles and air pockets from components of system 1001.

System 1001 is then primed with solvent. With valve 1031 open, solvent pump 1007 is operated to dispense solvent at a high flow rate into microfluidic chip 301 and system 1001 until residual alkane is displaced. Valve 1031 is then closed.

The integrity of filter 309 of microfluidic chip 301 is then tested with solvent. Second solvent pump 1007 is operated to dispense solvent through microfluidic chip 301 and optical cell 1029 at about 1200 microliters per minute, at about 600 microliters per minute, and at about 300 microliters per minute. The flow at each rate is sustained for a sufficient amount of time to obtain a stable pressure plateau for about 20 seconds each. Delays are performed between pressure pulses to allow the pressure to dissipate to the background level.

Reference values are then determined for optical cell 1029. The spectral light transmission through the cleaned flow cell of optical cell 1029, primed with solvent, is captured and stored as a white reference. The light source is blocked while a second spectral response is captured and stored as a dark reference.

The crude oil sample is then pre-injected into system 1001. All syringes are filled for a synchronous start. Valve 1017 is activated. First solvent pump 1003 and alkane pump 1005 are activated to introduce the crude oil sample and alkane, respectively, into microfluidic chip 301. Higher flow rates can be used until the heart of the crude oil slug reaches the mixer inlet of microfluidic chip 301 to save cycle time. In certain operations, solvent is added to the mixer of microfluidic chip 301 at a moderate rate to decrease fluid viscosity.

System 1001 is then flushed with solvent. Second solvent pump 1007 is operated to flush solvent through system 1001 to remove oil from microfluidic chip 301 and optical cell 1029. Crude oil sample, however, remains in the sample feed line to sample inlet port 303 of microfluidic chip 301.

A diluted crude oil run is then performed. All syringes are filled for a synchronous start. First solvent pump 1003 and second solvent pump 1007 are activated to urge the crude oil sample and solvent, respectively, into microfluidic chip 301. In certain operations, first solvent pump 1003 is operated to introduce crude oil into microfluidic chip 301 at a rate of about ten microliters per minute, while second solvent pump 1007 is operated to introduce solvent into microfluidic chip 301 at a rate within a range of about 400 microliters per minute to 1000 microliters per minute, depending on the type of crude oil sample. In one particular operation, flow is maintained for about five minutes. As the mixture is urged through microfluidic chip 301 and optical cell 1029, absorbance signals at a wavelength of about 600 nanometers are recorded over time. The duration of the run is sufficient so that a stable absorbance value is recorded for about three minutes.

System 1001 is then flushed with solvent. Second solvent pump 1007 is operated to flush solvent through system 1001 to remove oil from microfluidic chip 301 and optical cell 1029. Crude oil sample, however, remains in the sample feed line to sample inlet port 303 of microfluidic chip 301.

Microfluidic chip 301 is then primed with alkane. Alkane pump 1005 dispenses alkane at a high flow rate into microfluidic chip 301 and optical cell 1029 until residual toluene is displaced.

The integrity of filter 309 of microfluidic chip is then tested with alkane. Alkane pump 1005 is operated to dispense alkane through microfluidic chip 301 and optical cell 1029 at about 1200 microliters per minute, at about 600 microliters per minute, and at about 300 microliters per minute. The flow at each rate is sustained for a sufficient amount of time to obtain a stable pressure plateau for about 20 seconds each. Delays are performed between pressure pulses to allow the pressure to dissipate to the background level.

Reference values are then determined for optical cell 1029. The spectral light transmission through the cleaned flow cell of optical cell 1029, primed with alkane, is captured and stored as a white reference. The light source is blocked while a second spectral response is captured and stored as a dark reference.

A maltene separation run is then performed. All syringes are filled for a synchronous start. First solvent pump 1003 and alkane pump 1005 are activated to urge the crude oil sample and alkane, respectively, into microfluidic chip 301. In certain operations, first solvent pump 1003 is operated to introduce crude oil into microfluidic chip 301 at a rate of about ten microliters per minute, while alkane pump 1005 is operated to introduce alkane into microfluidic chip 301 at a rate of about 400 microliters per minute. In one particular operation, flow is maintained for about five minutes. As the mixture is urged through microfluidic chip 301 and optical cell 1029, absorbance signals at a wavelength of about 600 nanometers are recorded over time. The duration of the run is sufficient so that a stable absorbance value is recorded for about three minutes.

System 1001 is then cleaned. Valve 1031 is switched to the open position and second solvent pump 1007 is operated to urge solvent into microfluidic chip 301 at a rate of about 500 microliters per minute, urging solvent toward filter 309 of microfluidic chip 301 to dissolve asphaltene deposits. If solvent injection pressure exceeds about three bar, operation of second solvent pump 1007 is paused and only resumed if the pressure drops below about 2.5 bar. After substantially all asphaltene is dissolved and pressure is maintained at a normal level, solvent flow is maintained while first solvent pump 1003 operates at a flow rate of about 50 microliters per minute until crude oil in the sample feed line is displaced. First solvent pump 1003 and second solvent pump 1007 then operate at maximum flow rate as all valves are switched to ensure complete cleaning of system 1001 and to substantially fill system 1001 with clean solvent.

The integrity of filter 309 of microfluidic chip 301 is then tested with solvent. Second solvent pump 1007 is operated to dispense solvent through microfluidic chip 301 and optical cell 1029 at about 1200 microliters per minute, at about 600 microliters per minute, and at about 300 microliters per minute. The flow at each rate is sustained for a sufficient amount of time to obtain a stable pressure plateau for about 20 seconds each. Delays are performed between pressure pulses to allow the pressure to dissipate to the background level.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures.

What is claimed is:

1. A microfluidic chip, comprising:
an upper layer defining a sample inlet port, a solvent port, a waste port, a product port, a mixing channel, and a reactor channel, the mixing channel in fluid communication with the sample inlet port, the solvent port, and the reactor channel;
an intermediate layer defining a further channel in fluid communication with the reactor channel;
a membrane filter in fluid communication with the further channel, the membrane filter having an inlet side and an outlet side, wherein the waste port is in fluid communication with the inlet side of the membrane filter; and
a lower layer defining a product channel, the product channel in fluid communication with the outlet side of the membrane filter and the product port, and wherein the lower layer further defines a filter channel corresponding to the further channel, the filter channel in fluid communication with the outlet side of the membrane filter and the product channel.

2. The microfluidic chip of claim 1, wherein the lower layer comprises polyetheretherketone.

3. The microfluidic chip of claim 1, wherein at least one of the reactor channel and the further channel are serpentine in configuration.

4. The microfluidic chip of claim 1, wherein at least one of the reactor channel and the further channel are microfluidic channels.

5. The microfluidic chip of claim 1, wherein the upper layer and the intermediate layer comprise one of glass or fused silica.

* * * * *